(12) United States Patent
Le et al.

(10) Patent No.: US 8,945,933 B2
(45) Date of Patent: Feb. 3, 2015

(54) LIQUID CHROMATOGRAPHY-MASS SPECTROMETRY METHODS FOR MULTIPLEXED DETECTION AND QUANTITATION OF FREE AMINO ACIDS

(75) Inventors: Anthony Le, San Jose, CA (US); Tina Cowan, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 800 days.

(21) Appl. No.: 12/902,908

(22) Filed: Oct. 12, 2010

(65) Prior Publication Data

US 2011/0085983 A1 Apr. 14, 2011

Related U.S. Application Data

(60) Provisional application No. 61/250,774, filed on Oct. 12, 2009.

(51) Int. Cl.
*G01N 33/00* (2006.01)
*G01N 24/00* (2006.01)
*G01N 30/02* (2006.01)
*G01N 33/68* (2006.01)
*G01N 30/14* (2006.01)
*G01N 30/60* (2006.01)
*G01N 30/72* (2006.01)
*G01N 30/88* (2006.01)

(52) U.S. Cl.
CPC ............ *G01N 33/6806* (2013.01); *G01N 30/14* (2013.01); *G01N 30/6004* (2013.01); *G01N 30/7233* (2013.01); *G01N 33/6848* (2013.01); *G01N 2030/8818* (2013.01); *G01N 2500/10* (2013.01); *G01N 2800/04* (2013.01); *G01N 2800/52* (2013.01)
USPC ................ 436/86; 436/89; 436/173; 436/161

(58) Field of Classification Search
CPC . A61K 49/0056; A61K 49/14; A61K 49/146; A61K 31/223; A61K 38/05; A61K 38/06; A61K 47/183; G01N 33/68; G01N 33/6812; G01N 33/6818; G01N 33/6806; G01N 33/6851; G01N 33/6848; G01N 30/72; G01N 30/02; G01N 2030/027; G01N 2030/484; G01N 2030/468; G01N 2560/00; C07K 7/06; C07K 2/00; C07K 9/001; C07K 1/1075; C07K 1/18; C07K 5/0821
See application file for complete search history.

(56) References Cited

PUBLICATIONS

Piraud et al. "Ion-pairing reversed-phase liquid chromatography/ electrospray ionization mass spectrometric analysis of 76 underivatized amino acids of biological interest: a new tool for the diagnosis of inherited disorders of amino acid metabolism" Rapid Commun. Mass Spectrom., 2005, v. 19, pp. 1587-1602.*
Armstrong et al. "Analysis of 25 underivatized amino acids in human plasma using ion-pairing reversed-phase liquid chromatography/ time-of-flight mass spectrometry", Rapid Commun. Mass Spectrom., 2007, v. 21, pp. 2717-2726.*

(Continued)

*Primary Examiner* — Yelena G Gakh
(74) *Attorney, Agent, or Firm* — Foley & Lardner LLP; Cliff Z. Liu

(57) ABSTRACT

The present invention provides liquid chromatography-mass spectrometry methods and kits for the specific, sensitive and rapid detection as well as quantitation of free amino acids in samples following High Pressure Liquid Chromatography (HPLC) separation.

12 Claims, 3 Drawing Sheets

(56) References Cited

PUBLICATIONS

Figure 1:
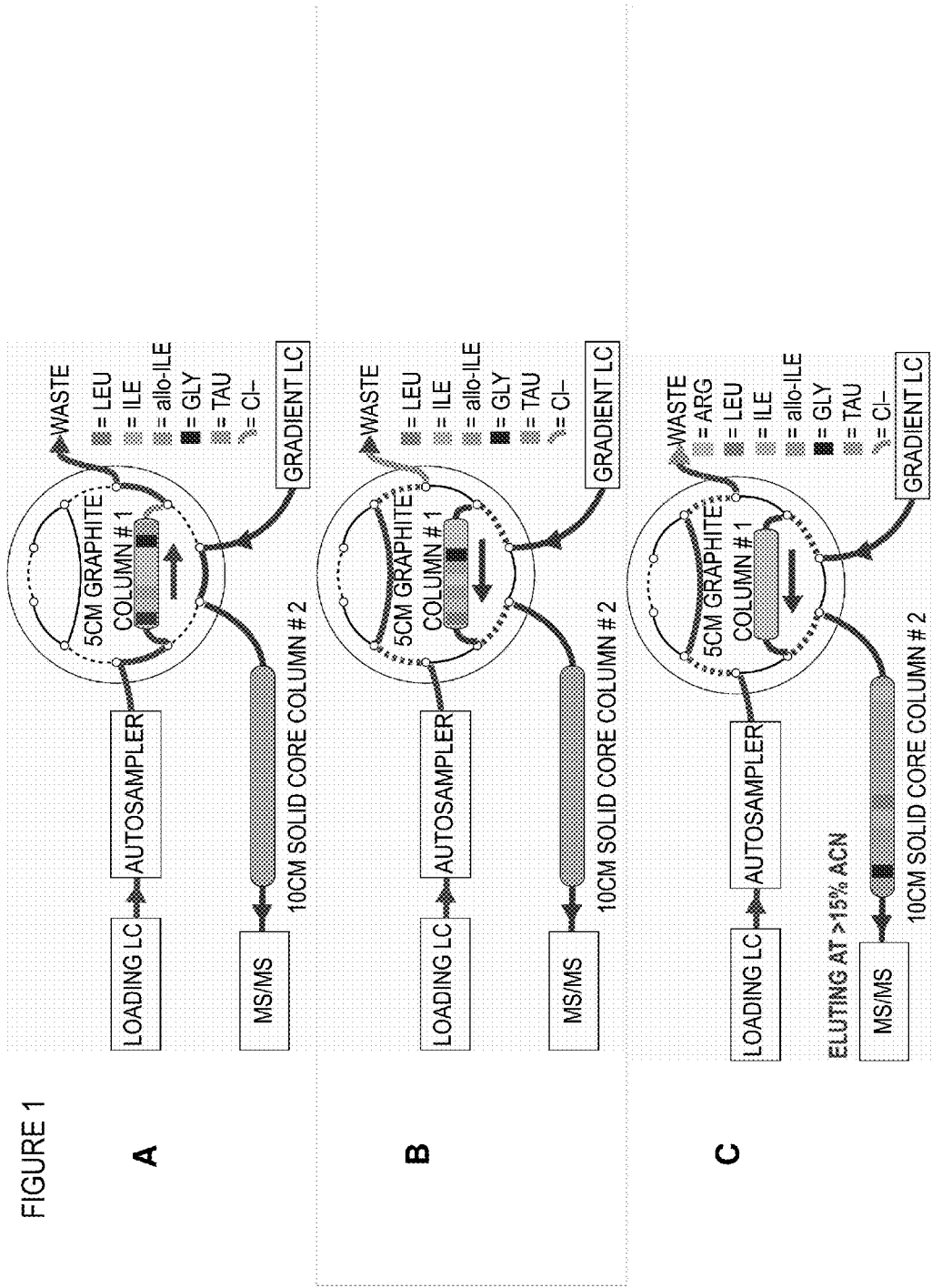

Shama et al. "Quantitative analysis of 17 amino acids in the connective tissue of patients with pelvic organ prolapse using capillary electrophoresis—tandem mass spectrometry", J. Chromatogr. B, 2008, v. 865, pp. 18-24.*

Ross "HPLC Columns for the Retention of Very Polar Molecules", Technical Bulletin, 2002, pp. 1-7.*

"Method Development Guide for HypercarbTM Columns", ThermoElectron Corporation, 2004, 32 pages.*

AEvarsson, et al., "Crystal structure of human branched-chain α-ketoacid dehydrogenase and the molecular basis of multienzyme complex deficiency in maple syrup urine disease", Structure, vol. 8, No. 3, pp. 277-291, (2000).

Bruins, Andries, "Mechanistic aspects of electrospray ionization", Journal of Chromatography A, 794, pp. 345-357, (1998).

Dietzen, et al., "Rapid comprehensive amino acid analysis by liquid chromatography/tandem mass spectrometry: comparison to cation exchange with post-column ninhydrin detection", Rapid Communications in Mass Spectrometry, 22, pp. 3481-3488, (2008).

Freeto, et al., "A rapid ultra performance liquid chromatography tandem mass spectrometric method for measuring amino acids associated with maple syrup urine disease, tyrosinaemia phenylketonuria", ann. Clin. Biochem., 44: pp. 474-481, (2007).

Lim, et al., "Electronic Interaction Chromatography on Porous Graphitic Carbon. Separation of [99mTc]Pertechnetate and Perrhenate Anions", Biomedical Chromatography, vol. 3, No. 2, pp. 92-93, (1989).

Piraud, et al., "ESI-MS/MS analysis of underivatised amino acids: a new tool for the diagnosis of inherited disorders of amino acid metabolism. Fragmentation study of 79 molecules of biological interest in positive and negative ionization mode", Rapid Communications in Mass Spectrometry, 17: pp. 1297-1311, (2003).

Piraud, et al., "A new reversed-phase liquid chromatographic/tandem spectrometric method for analysis of underivatised amino acids: evaluation for the diagnosis and the management of inherited disorders of amino acid metabolism", Rapid Communications in Mass Spectrometry, 19: pp. 3287-3297, (2005).

Spackman, et al., "Automatic recording apparatus for use in the chromatography of amino acids", Analytical Chemistry, vol. 30, No. 7, pp. 1190/1206, 1958.

* cited by examiner

LIQUID CHROMATOGRAPHY-MASS SPECTROMETRY METHODS FOR MULTIPLEXED DETECTION AND QUANTITATION OF FREE AMINO ACIDS

RELATED APPLICATION

This application claims priority and other benefits from U.S. Provisional Patent Application Ser. No. 61/250,774, filed Oct. 12, 2009, entitled "Liquid Chromatography-Mass Spectrometry Methods For Multiplexed Detection and Quantitation of Free Amino Acids". Its entire content is specifically incorporated herein by reference.

TECHNICAL FIELD OF THE INVENTION

The present invention relates generally to the field of qualitative and quantitative analysis. In particular, the invention relates to the analysis of amino acids in biological as well as nonbiological samples using liquid chromatography-tandem mass spectrometry.

BACKGROUND

Amino acids are the building blocks of proteins, and certain amino acids participate in critical biochemical and cellular processes essential for the growth, development and survival of an organism. Qualitative and quantitative amino acid analysis is, therefore, an important analytical and diagnostic tool in a wide variety of clinical, biopharmaceutical and agriculture applications as well as in metabolic and metabolomic research studies.

The presence, absence, identity, amount or modification of an endogenous amino acid as well as its presence and amount in comparison to other amino acids (i.e., the overall profile of free amino acids) are important parameters in assessing a subject's metabolic state. Aberrant amino acid levels or increased/decreased levels of certain amino acids in comparison to other amino acids can indicate a metabolic disturbance requiring precise and accurate detection and quantitation so that an appropriate intervention can be devised. Therapeutic interventions of metabolic disturbances often include dietary restriction, but can also involve the administration of vitamins and/or other pharmacological agents. Depending on the condition, these treatments may be essential for a patient's survival and optimal mental development.

The qualitative and quantitative analysis of free amino acids in biological fluids and tissues is central to the diagnosis and management of a wide variety of metabolic disturbances including primary amino acid enzymopathies (e.g., phenylketonuria, maple syrup urine disease) and disorders of amino acid transport (e.g., cystinuria). Comprehensive metabolic profiling gives a snapshot of the current physiological state of a subject or experimental organism and, besides uncovering primary metabolic disturbances, is instrumental in evaluating a subject's nutritional status, organ function and compliance with metabolic therapies.

A number of semi-automated High Pressure Liquid Chromatography (HPLC) systems for amino acid analysis have been developed for use in the clinical setting, using pre-column and/or post-column derivatization techniques. The traditional and most widely used approach is based on separation by cation-exchange HPLC and post-column derivatization with ninhydrin, a method whereby negatively charged interferents (e.g., chloride, phosphate) are eluted with the void volume (Spackman et al, 1958). Despite overall excellent performance with simple sample preparation, good linearity over a wide dynamic range, and baseline separation of compounds, this method suffers from long sample analysis times as well as the use of costly reagents and buffers. Alternatively, pre-column derivatization with various reagents such as o-phthalaldehyde (OPA) and separation by reversed-phase HPLC achieve high sensitivity and fast analysis times, but require extensive sample preparation. Furthermore, this approach is generally relegated for the analysis of matrices that have few interferents, such as urine. Since the mode of detection of all these methods is based on spectrophotometry, their performance particularly with respect to specificity is generally compromised by potential interferences from co-eluting molecules that cannot adequately be identified or detected by spectrophotometric detection alone.

More recently, methods utilizing tandem mass spectrometry (MS/MS) for amino acid analysis in physiological samples have been reported (Freeto et al, 2007, Dietzen et al, 2008, Casetta et al, 2000, Piraud et al, 2003, Piraud et al, 2005a, Piraud et al, 2005b). These share features with the traditional pre-column and post-column methods, and include analysis of both derivatized and underivatized molecules. While all methods represent significant improvements in specificity and analysis times, those involving separation of derivatized (i.e., butylated) molecules by reversed-phase HPLC are associated with lengthy sample preparation and decreased reproducibility stemming from the derivatization procedure itself. In addition, preparative and chromatographic conditions do not favor the removal of negatively charged molecules (e.g., chloride, phosphate), which lead to ion suppression and consequently diminished sensitivity for some molecules.

Reversed-phase HPLC separation of underivatized amino acids in the presence of the ion-pairing agent tridecafluoroheptanoic acid effectively removes interfering molecules and reduces ion suppression, but the associated solvent conditions still result in reduced sensitivity for the most nonpolar molecules, notably glycine, taurine and s-sulfocysteine, due to poor ionization in the detector (Piraud et al, 2005b). In some cases problems with imprecision are overcome by the inclusion of one or more stable-isotope internal standards, but these reagents are costly and not commercially available for all amino acids.

Improved methods for the sensitive and specific, yet quick and cost-effective analysis of amino acids, in particular of the clinically relevant amino acids, in biological fluids and tissues would greatly facilitate the reliable and rapid detection of metabolic disturbances, assessment of organ function and nutritional status of a subject and are, therefore, urgently needed. Those improved methods would also be valuable for evaluating the amino acid content in nonbiological samples to assess parameters such as quality and purity of a sample.

SUMMARY

The present invention features liquid chromatography-mass spectrometry methods and kits for the specific, sensitive and rapid detection as well as quantitation of free amino acids in biological fluids, tissues, and other sample matrices following High Pressure Liquid Chromatography (HPLC) separation. The methods and kits allow the reliable detection as well as quantitation of the clinically relevant amino acids, even the most non-polar ones, and find wide-spread application in various areas such as diagnosing metabolic disorders, therapeutic drug monitoring, drug screening and general testing for purity and/or quality of a sample, regardless whether the sample is of biological or nonbiological origin.

In certain embodiments of the invention, separation of amino acids is achieved using a series of two chromatographic columns. In certain embodiments of the invention, compounds are eluted off of the first chromatographic column in a flow-reverse direction. In some embodiments of the invention, the sample can be a biological fluid consisting of or containing blood, serum, plasma, lymph fluid, amniotic fluid, saliva, cerebrospinal fluid, lacrimal fluid, mucus, urine, sputum, sweat, or a combination thereof. In other embodiments of the invention, the sample can be a biological tissue consisting of or containing skeletal muscle tissue, liver tissue, lung tissue, kidney tissue, myocardial tissue, brain tissue, or a combination thereof.

In some embodiments, one or more internal standards can be added to the sample prior to sample preparation and/or chromatographic separation. In yet another aspect, the invention provides a method of diagnosing a metabolic disorder in a subject, including the steps of obtaining a sample from a subject; deproteinizing the sample to obtain free amino acids; separating the amino acids by liquid chromatography; ionizing the amino acids to generate ions; detecting ions by selected reaction monitoring (SRM); and quantifying the concentration of molecular ions and fragment ions captured by the mass detector wherein an elevated, reduced or otherwise abnormal level of one or more amino acids in the sample relative to the level in a reference sample is an indication that the subject has, or is at risk of developing, a metabolic disorder. The metabolic disorder can be any inherited or acquired disturbance in amino acid metabolism or transport, including phenylketonuria, maple syrup urine disease, cystinuria, or any other condition involving disturbances in endogenous amino acid concentrations. The reference population can be from subjects not having, not suspected of having, or not at risk of developing a metabolic disorder.

In some embodiments, one or more amino acids can be measured simultaneously in a multiplexed fashion. In preferred embodiments, the methods and kits of the invention are carried out using a tandem mass spectrometer.

In yet another embodiment, the invention provides a method of evaluating a subject's response to a therapeutic agent or therapeutic intervention. The method includes the steps of obtaining a biological sample from a subject; deproteinizing the sample to obtain free amino acids; separating the amino acids by liquid chromatography; ionizing the amino acids to generate ions; detecting ions by selected reaction monitoring (SRM); and quantifying the concentration of molecular ions and fragment ions captured by the mass detector. Specific alterations of levels of certain amino acids in a subject undergoing therapy compared to levels prior to the implementation of therapy may indicate hereby that the subject is responding to the treatment, while unchanged amino acid levels before and after therapeutic intervention may indicate that the subject is not responding to the treatment.

In yet another embodiment, the invention provides a method of identifying a candidate agent that modulates aberrant amino acid levels in a non-human model organism or in an in-vitro cell system.

In yet another embodiment, the invention provides a method for evaluating amino acid concentrations in research samples derived from studies including those of experimental animals that might be of mammalian or non-mammalian origin, cell culture products, tissue extracts, and synthetic mixtures.

In yet another aspect, the invention provides a kit for detecting and quantitating free amino acids. In some embodiments of the kit, the kit can also contain computer software useful for detecting, quantifying and reporting one or more amino acids. In further embodiments of the kits, the kit can also contain one or more internal standards useful in quantifying one or more amino acids, particularly in quantifying one or more clinically relevant amino acids.

In yet other embodiments, the invention provides methods to determine the amino acid content of a biological or non-biological sample for the purpose of assessing parameters including, but not limited to, purity or quality of the sample. In one particular embodiment, the purity of an amino acid or amino acid mixture might be assessed that resulted from enzymatic, chemical or other synthesis, or resulted from a purification or manufacturing process.

The above summary is not intended to include all features and aspects of the present invention nor does it imply that the invention must include all features and aspects discussed in this summary.

INCORPORATION BY REFERENCE

All publications, patent applications and patents mentioned in this specification are herein incorporated by reference to the same extent as if each individual publication or patent application was specifically and individually indicated to be incorporated by reference.

DRAWINGS

The accompanying drawings illustrate embodiments of the invention and, together with the description, serve to explain the invention. These drawings are offered by way of illustration and not by way of limitation; it is emphasized that the various features of the drawings are not to-scale.

FIG. 1 shows an example of the liquid chromatography configuration for sample cleanup and amino acid separation, in accordance with an embodiment of the present invention: (A) sample is loaded onto Column 1, where amino acids are retained and chloride ions (pink) are eluted to waste; (B): solvent flow is reversed and amino acids are eluted in a gradient of 14-45% acetonitrile; (C): chromatographic separation occurs on Column 2 and amino acids are eluted to the mass spectrometer in acetonitrile conditions favoring subsequent ionization and detection.

Figure 2:
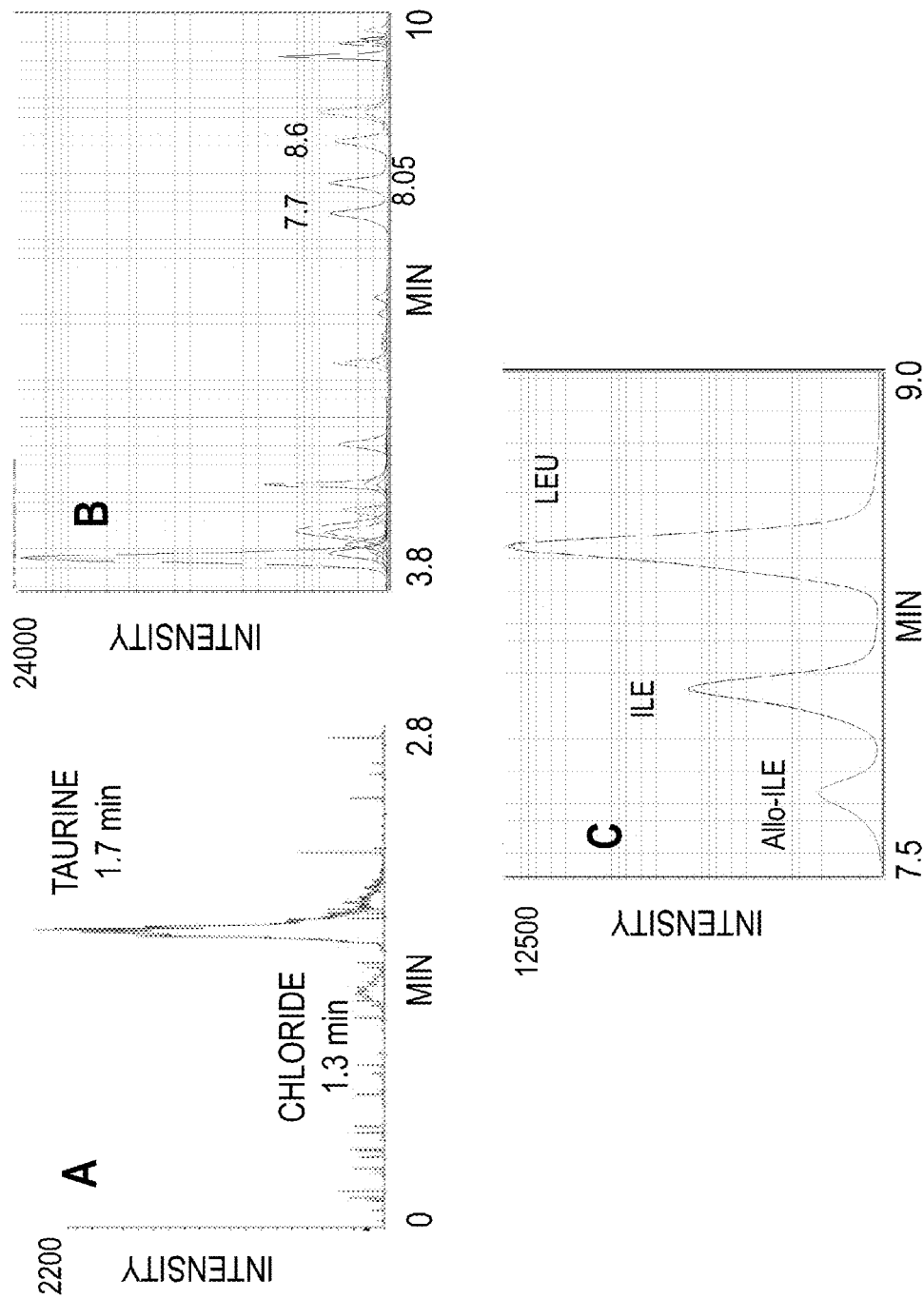

FIG. 2 shows an example of chromatographic separation and mass spectrometric identification of free amino acids, in accordance with an embodiment of the present invention: (A) separation of chloride ion from the first eluting amino acid, taurine; (B): full chromatogram for 32 amino acids; (C): baseline resolution of alloisoleucine, leucine, and isoleucine.

Figure 3:
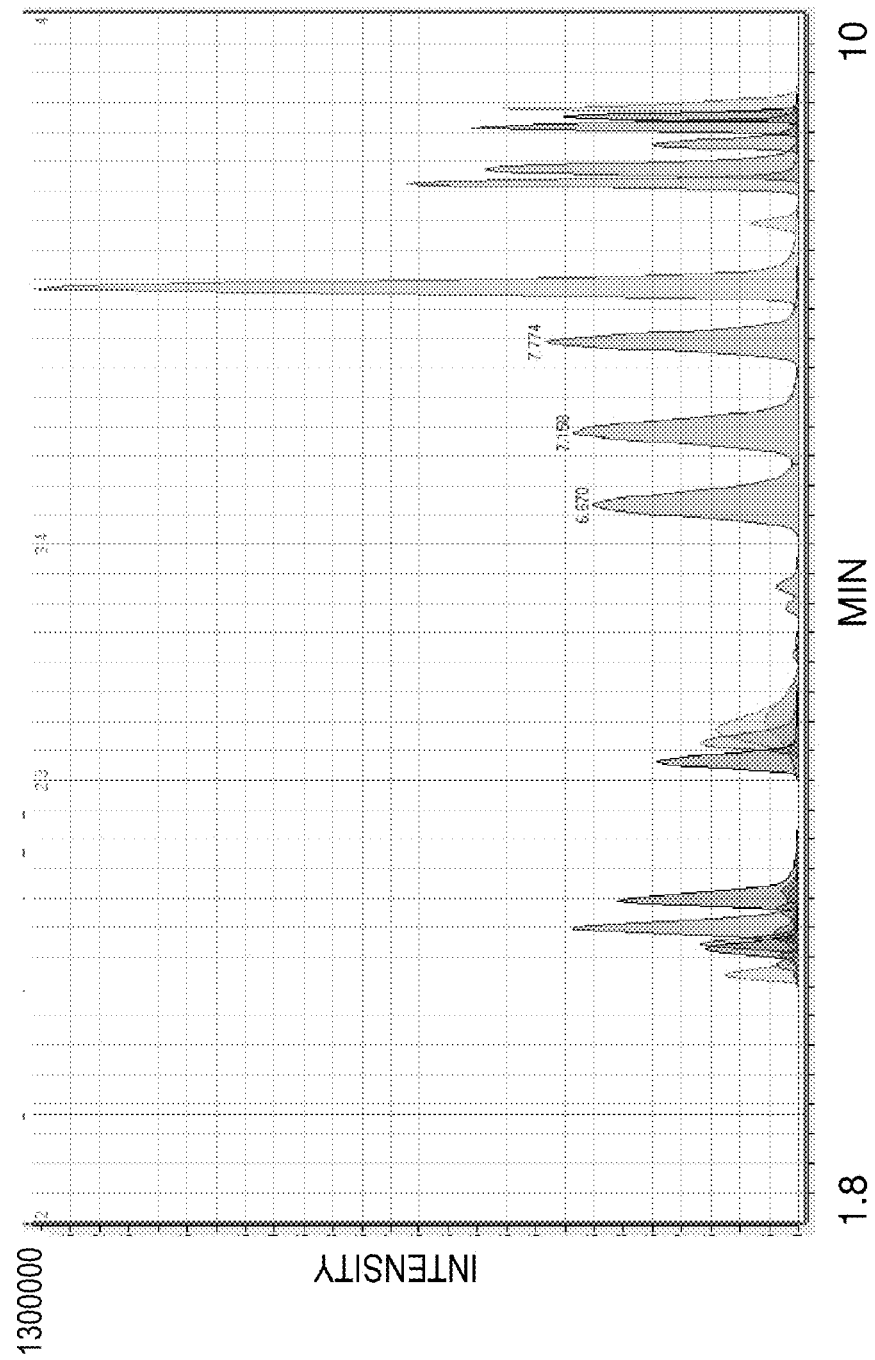

FIG. 3 shows another example of chromatographic separation and mass spectrometric identification of free amino acids, in accordance with an embodiment of the present invention: in this chromatogram the separation of taurine, aspartic acid, hydroxy-proline, asparagine, serine, glutamine, sarcosine, glutamic acid, Glycine, threonine, proline, citrulline, cystine, alanine, homocitrulline, cystathionine, valine, methionine, tyrosine, β-alanine, ethanolamine, alloisoleucine, isoleucine, leucine, phenylalanine, S-aminoethylcysteine, tryptophan, histidine, ornithine, homocystine, lysine, and arginine was achieved.

DEFINITIONS

The practice of the present invention may employ conventional techniques of analytical chemistry and biochemistry, which are within the capabilities of a person of ordinary skill in the art. Such techniques are fully explained in the literature. For definitions, terms of art and standard methods known in the art, see, for example, W. V. Ligon "Liquid Chromatography Mass Spectrometry", Encyclopedia of Materials: Science and Technology (2001), pp. 4502-4511; A. P. Bruins "Liquid chromatography-mass spectrometry with ionspray and electrospray interfaces in pharmaceutical and biomedical research", Journal of Chromatography 554 (1991), pp. 39-46; W. M. A. Niessen & A. P. Tinke "Liquid chromatography-mass spectrometry: General principles and instrumentation", Journal of Chromatography A 703 (1995), pp. 37-57; and W. M. A. Niessen "Chromatography-MS, Methods", Encyclopedia of Spectroscopy and Spectrometry (2004), pp. 293-300. Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise.

The term "amino acid", as used herein, means any molecule that includes an alpha-carbon atom covalently bonded to an amino group and an acid group, whereby the acid group may include a carboxyl group. "Amino acid" includes L-amino acids and D-amino acids and any isomers and derivatives thereof. The 20 proteinogenic amino acids that represent the building blocks of proteins differ in their side-chain groups, which influence the amino acids' chemical reactivity, ionic charge, relative hydrophilicity or hydrophobicity and polarity.

The term "metabolic disorder", as used herein, means any inherited or acquired metabolic condition that occurs when certain amino acids are either not degraded properly in the body or not produced properly by the body, resulting in the accumulation of amino acids and/or their metabolites and possibly the deficiency of other substances.

The terms "quantify" and "quantitate" as well as "quantification" and "quantitation", are used interchangeably herein.

The terms "analyzing", "assessing", "determining", "measuring", as used herein, include qualitatively detecting, quantitatively detecting or qualitatively and quantitatively detecting.

The term "flow-reverse", as used herein, means that the sample enters the first chromatographic column from the inlet port of said column, after which the flow is reversed and the sample is then eluted back through said column, which has remained in the same position throughout the separation process, with a solvent or solvent mixture, and eventually discharged at the inlet port of the column.

The term "subject", as used herein, refers to a member of a species of mammalian origin, including but not limited to a human, mouse, rat, cat, goat, sheep, horse, hamster, ferret, pig, dog, guinea pig, rabbit or primate.

The term "sample", as used herein, encompasses any specimen that originates from a biological or nonbiological source, human or non-human source, mammalian or non-mammalian source. Exemplary samples, which the methods of the present invention can be applied to, include, but are not limited to, biological fluids and tissues from a human or non-human (animal) source such as blood, urine, saliva, liver tissue, samples from cell cultures and so forth. Exemplary samples further include non-biological samples that consist of or contain a food, food component or pharmacological agent and that might be analyzed for the purposes of assessing the purity of a sample and/or for assessing the concentration of ingredients.

The term "pharmacological agent", as used herein, refers to a drug, molecule, hormone, nucleic acid, protein, amino acid, composition or other substance that provides a therapeutic effect. A therapeutic effect refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest, reduction, or elimination of the progression of a disease manifestation.

DETAILED DESCRIPTION

The present invention features liquid chromatography-mass spectrometry methods and kits for the specific, sensitive and rapid detection as well as quantitation of free amino acids in biological fluids and tissues following High Pressure Liquid Chromatography (HPLC) separation. Advantageously, these methods and kits exhibit high sensitivity and specificity for most, if not all clinically relevant amino acids, even the most non-polar ones, with linear dynamic ranges of over three orders of magnitude at micromolar range (1-2000 micromolar) with short sample preparation (less than ten minutes), short analysis time (less than ten minutes) as well as baseline resolution of structural isomers. These methods and kits have a wide variety of applications in various areas such as diagnosing metabolic disorders, therapeutic drug monitoring and purity testing.

In application of the methods and kits of the present invention metabolic profiles can be obtained for a subject which can be utilized to assess the health status of that subject particularly to confirm the presence or absence of metabolic disorders. In further application of the methods and kits of the present invention, a subject's compliance with dietary restrictions can be assessed and monitored. In further application of the methods and kits of the present invention, a subject's response to a therapeutic agent can be evaluated and therapeutic success or failure can be monitored and managed. In further application of the methods and kits of the present invention, the purity of a sample following synthesis or following a purification process can be assessed.

Separation of Amino Acids by High Pressure Liquid Chromatography

High pressure liquid chromatography (HPLC) is a form of column-based chromatography that is routinely used in analytical chemistry to separate, identify or detect and quantify molecules. HPLC utilizes a column that holds chromatographic packing material (stationary phase), a pump that moves the mobile phase(s) through the column, and a detector that detects the abundance of the molecules and shows their retention on the chromatographic column in relation to the elapsed time (retention time). Retention times vary depending on the interactions between the stationary phase, the molecules being analyzed, and the solvent(s) used. A sample containing the analyte or analytes is injected into the mobile phase manually or by an automated autosampler. The polarity of the analyte, the stationary phase of the column(s) used and the mobile phase(s) determine the retention time of the analyte as well as its separation from interferences and extent of quantifiability. Amino acid separation using HPLC may be performed with any commercially available LC apparatus using automated or manual sample injection and adjustable, consistent and reproducible solvent flow rates.

Chromatographic Columns.

Columns suitable for liquid chromatography contain packing materials that include very small and usually spherical particles, e.g., silica particles, having a diameter of 3-50 microns and a pore size of 100-1000 angstroms. Commonly, HPLC is performed with a stationary phase attached to the outside surface of such small particles; such stationary phase may provide that surface hydrophobic properties or enable ion change or ion pairing. A chromatographic column typically includes two ports, one inlet port for receiving a sample and one outlet port for discharging an effluent that may or may not include the sample.

In some embodiments of the present invention, the one or more amino acids in a sample enter a column from the inlet port, are then eluted with a solvent or solvent mixture, and eventually discharged at the outlet port. In preferred embodiments, one or more amino acids in a sample enter a column from the inlet port whereafter the flow across said column is reversed and one or more amino acids are then eluted with a solvent or solvent mixture, and eventually discharged back at the inlet port (flow-reverse). Using a chromatographic column flow-reverse, and specifically using the first chromatographic column of two successive chromatographic columns flow-reverse, proved beneficial in delaying the elution of hydrophilic amino acids and in improving their ionization in the mass detector, leading to increased analytical sensitivity (see FIG. 1).

Different solvents or solvent mixtures may be selected for eluting the amino acids. For example, liquid chromatography may be performed using a gradient mode with differing amounts of solvents in the mixture, an isocratic mode with continuously fixed amounts of solvents in the mixture or a partially isocratic, partially gradient mixed mode. Suitable solvents and solvent mixtures include sodium or lithium buffers (for cation exchange HPLC) or acetonitrile (for reverse phase HPLC).

The internal diameter of an HPLC column is an important parameter that influences the detection sensitivity and separation selectivity. Column dimensions in preferred embodiments of the present invention include a column internal diameter of 2.1-3.0 mm and a column length of 5-10 cm.

Column Packing Materials for Liquid Chromatography.

Liquid chromatography is based on the principle that an analyte is adsorbed to a stationary phase and eventually desorbed and eluted with the mobile phase into a detection unit for proper detection and/or quantitation. The choice of both stationary and mobile phase greatly influences the success of chromatographic separation.

Reversed Phase Liquid Chromatography.

Reversed phase HPLC(RP-HPLC or RPC) has a non-polar stationary phase and an aqueous, moderately polar mobile phase. One common stationary phase is a silica which has been treated with R-Me$_2$SiCl, where R is a straight chain alkyl group such as C$_{18}$H$_{37}$ (octadecyl, C18) or C$_8$H$_{17}$ (octyl, C8). With these stationary phases, retention time is longer for molecules which are more non-polar, while polar molecules elute more readily. The mobile phase is generally a binary mixture of water and a miscible polar organic solvent like methanol, acetonitrile or tetrahydrofuran (THF). Reversed phase chromatography is based on partition and is typically used for separations by non-polar differences.

Normal Phase Liquid Chromatography.

In contrast to reversed phase HPLC, normal phase HPLC (NP-HPLC) uses a polar stationary phase and a non-aqueous, non-polar mobile phase, and works effectively for separating analytes readily soluble in non-polar solvents. The analyte associates with and is retained by the polar stationary phase until final elution. Typical stationary phases for normal phase chromatography are silica or organic moieties with cyano- and/or amino-functional groups. In NP-HPLC, the most non-polar molecules elute first and the most polar molecules elute last. The mobile phase consists of a very nonpolar solvent like hexane or heptane mixed with a slightly more polar solvent like isopropanol, ethyl acetate or chloroform. Retention increases, as the amount of nonpolar solvent in the mobile phase increases. NP-HPLC is based on adsorption and is typically employed for the analysis of solutes readily soluble in organic solvents, based on their polar differences such as amines, acids, metal complexes, etc.

Liquid Chromatography Using Graphitic Carbon-Based Column Packing Materials.

Graphite can exert a polar retentive effect and can interact by an electron-transfer mechanism with molecules that contain lone-pair electrons or aromatic ring electrons. Graphite can function equally well as an electron donor as well as an electron acceptor and, therefore, separation based on graphitic carbon-based column packing materials is achieved, at least partially, based on ion pair formation {Lim, 1989}. In preferred embodiments of the present invention, a graphite carbon column was used as column 1, while a C18-column was used as column 2.

Ion Exchange Chromatography.

Since amino acids, by definition, contain at least one amino-group and one carboxyl acid group, they are ionizable and consequently carry a—positive or negative—charge, when the pH of the mobile phase differs from the amino acid's pKa. Below the neutral pH of 7.0, amino acids with primarily basic groups (e.g., amino groups) are positively charged, whereas above the neutral pH of 7.0, amino acids with primarily acidic groups (e.g., carboxylic acid groups) are negatively charged. The 20 proteinogenic amino acids that represent the building blocks of proteins differ in their side-chain groups, which influence the amino acids' chemical reactivity, ionic charge, relative hydrophilicity or hydrophobicity and polarity. Ion-exchange chromatography is a process that allows the separation of ions and polar molecules based on the charge properties of the analytes. Charged amino acids may be either acidic or basic.

The stationary phase surface displays ionic functional groups (R—X) that interact with analyte ions of opposite charge. This type of chromatography is further subdivided into cation exchange chromatography and anion exchange chromatography. The target analytes (anions or cations) are retained on the stationary phase but can be eluted by increasing concentrations of similarly charged species that will displace the analyte ions from the stationary phase. For example, in cation exchange chromatography, the positively charged analyte could be displaced by the addition of positively charged sodium ions.

Ion Pairing Chromatography.

Similar to ion-exchange chromatography, ion pairing chromatography utilizes the ionizability and charge properties of the analytes for the chromatographic separation. However, instead of exchanging ions, ion-pairing systems are established using perfluorinated carboxylic acids such as tridecafluoroheptanoic acid (TDFHA) or trifluoroacetic acid (TFA) as mobile phase constituents and a stationary phase that can accept or donate electrons or both. Specifically, ion pairing chromatography can be used to separate ionic analytes on a reversed-phase column in order to suppress the ionic characteristic of charged organic compounds. Ion pair reagents have a charge opposite of the analytes and a hydrophobic region to interact with the stationary phase. The charge of the absorbed ion pair reagent interacts electrostatically with the charge of the analytes. As an example, amines can produce a serious tailing chromatographic peak on a reversed phase column, while addition of an ion pair agent such as trifluoroacetic acid curtails tailing. With advances in column phases and a better selection of ion pair reagents, ion pair chromatography not only sharpens chromatographic peaks but also modulates the retention of ionic analytes on reverse-phase columns. Typical ion pair reagents include tetra-alkylammonium ions and perfluorinated organic acids. The type of ion pair reagent, the concentration of ion pair reagent, the type of organic modifier in the mobile phase, the concentration (gradient) of the organic modifier, and the proper selection of the columns are critical to a successful ion pair chromatography experiment. In preferred embodiments, ion pair chromatography was used.

HPLC-Mass Spectrometry Analysis.

Liquid chromatography coupled to mass spectrometry, particularly to tandem mass spectrometry (LC-MS/MS), has become an important tool in biomedical analysis, particularly, since it can circumvent problems due to interferents that often present themselves in the course of spectrophotometric detection. Most often interferences result, when molecules other than the analyte(s) exhibit a UV absorption spectrum that is similar to or even identical to the UV spectrum of the analyte(s).

In general, a mass spectrometer includes the following components: a sample inlet, an ion source, a collision cell, a mass analyzer, a detector, a vacuum, instrument-control and data analysis software. In LC-MS/MS, upon separation by LC, analytes are ionized, while transferred to a gaseous phase, then directed into an electric and/or magnetic field and ultimately detected as a result of their mass-to-charge ratio (m/z ratio). A number of different ionization techniques can be used in order to transfer the analytes from the liquid phase to the gaseous phase, to enable their introduction to the mass spectrometer. One of the most common interfaces is electrospray ionization (ESI) using an electron beam, which provides soft ionization and has the ability to ionize a wide variety of different molecules. ESI mass spectrometry can be divided into three steps: (i) nebulization of a sample solution into electrically charged droplets, (ii) liberation of ions from droplets, and (iii) transportation of ions from the atmospheric pressure ionization source region into the vacuum and mass analyzer of the mass spectrometer {Bruins, 1999}.

Internal Amino Acid Standards.

In some embodiments, one or more internal standards, representing the types of amino acids that might be present in a particular biological sample, can be added to the biological sample prior to sample preparation and/or sample injection. It is important to note that all internal standards used in the methods and kits of the present invention are unlabelled, in contrast to other methods requiring the use of stable-isotope internal standards. This significantly reduces the costs otherwise associated with the use of these internal standards, and also overcomes difficulties arising from the fact that stable-isotope standards are not commercially available for every amino acid of interest.

Tandem Mass Spectrometry.

In tandem mass spectrometry, two mass analyzers are linked in series via a collision cell. The first mass analyzer is used to select the ion of interest. The selected ion of interest is then transferred to the collision cell, where it is fragmented by collisions with an inert gas. The second mass analyzer is then used to scan for and detect all charged molecules and molecule fragments in accordance to their m/z ratios.

Mass Spectrometry Data Presentation and Analysis.

Mass spectrometry data are typically recorded in a mass spectrum or mass chromatogram, representing the distribution of the various molecules or molecule fragments, their mass-to-charge, retention time and so forth.

Sample Preparation.

Samples, in particular biological samples such as blood, serum, plasma, lymph fluid, amniotic fluid, saliva, cerebrospinal fluid, lacrimal fluid, mucus, urine, sputum, sweat, skeletal muscle tissue, liver tissue, lung tissue, kidney tissue, may be processed prior to analysis by LC chromatography-mass spectrometry in order to purify and/or enrich the amino acids present in a sample. Various procedures may be used for this purpose depending on the type of sample matrix including, but not limited to, filtration, precipitation, centrifugation, combinations thereof and the like. Following sample preparation, the sample is subjected to chromatographic separation, in particular by HPLC, and mass spectrometry, in particular by tandem mass spectrometry.

Utility of the Present Invention

Metabolic Profile.

The metabolic state of a subject can be reflected by a metabolic profile, which outlines the presence, absence, identity, amount or modification of an endogenous amino acid as well as its presence and amount in comparison to other amino acids, as these are important parameters in assessing a subject's health and metabolic state. Aberrant amino acid levels or increased/decreased levels of certain amino acids in comparison to other amino acids can indicate a metabolic disturbance and require appropriate intervention.

Diagnosis of Metabolic Disorders.

The methods and kits described herein can be used to obtain a metabolic profile of a subject to potentially diagnose metabolic disorders. From a pathophysiological perspective, metabolic disorders can be separated into three diagnostically useful groups {Fernandes et al., 1990}: (i) Metabolic disorders that give rise to intoxication, where inborn errors of metabolism lead to an acute or progressive intoxication from the accumulation of toxic compounds, in the body, e.g., maple syrup urine disease; (ii) metabolic disorders involving energy metabolism, e.g., mitochondrial defects, with symptoms resulting from a deficiency in energy production or utilization within liver, myocardium, muscle, brain and other tissues; and (iii) metabolic disorders involving complex molecules, e.g., inborn errors of cholesterol synthesis. While their specific symptoms vary, most metabolic disorders are characterized by some neurological involvement and potentially mental deterioration necessitating early and reliable diagnosis and disease management. Specific, sensitive and rapid detection as well as quantitation of free amino acids, as provided by the present invention, will be highly instrumental in the reliable evaluation and management of all types of metabolic diseases.

Monitoring of Compliance with Dietary Restrictions.

The methods and kits of the present invention can also be utilized to determine a subject's compliance with dietary restrictions that were prescribed due to the diagnosis and/or existence of a metabolic disorder in order to normalize aberrant amino acid levels, with or without simultaneous pharmacological intervention. Once an amino acid-based metabolic disorder has been diagnosed, dietary restrictions and/or other therapeutic interventions are implemented The continuous qualitative and quantitative analysis of amino acids in biological samples and/or tissues is instrumental in monitoring compliance with dietary restrictions and in controlling the therapeutic success of the chosen intervention, which will be evidenced by a gradual normalization of amino acid levels following treatment, in comparison to the previously aberrant amino acid levels. For monitoring purposes, samples will be taken from a subject prior to onset of dietary restriction and at appropriate time points (days, weeks or months) following onset of dietary restriction; those samples will be analyzed in comparison to test for a change in amino acid levels.

Therapeutic Monitoring.

Furthermore, the methods and kits of the present invention can be utilized to evaluate and monitor a subject's response to treatment with a pharmalogical agent that has been prescribed to treat the subject's metabolic disorder, and to monitor as well as manage therapeutic failure or success. For monitoring purposes, samples will be taken from a subject prior to onset of treatment and at appropriate time points (days, weeks or months) following treatment; those samples will be analyzed in comparison to test for a change in amino acid levels.

Drug Screening and Drug Development.

Furthermore, the methods and kits of the present invention are instrumental in drug screening and drug development to identify, detect and quantify the effect of experimental pharmacological agents for potential use in the treatment and/or management of metabolic disorders. Experimental compounds that might be useful in preventing and/or treating metabolic disorders can be evaluated in model organisms including rodent and invertebrate models and in-vitro cell systems by assessing their normalizing effect on aberrant amino acid levels.

General Sample Testing for Assessing Purity, Quality and Other Parameters.

Additionally, the methods and kits of the present invention can be utilized in assessing, for example, the purity of a sample following synthesis or following a purification or manufacturing process, including the analysis of cell culture media, the analysis of specimen following in-vitro testing in cell culture or following in-vivo testing in an experimental animal model. Furthermore, the methods and kits of the present invention can be valuable tools for the study of metabolism and the regulation of metabolism by genetic factors in the course of metabolic and metabolomic studies.

Amino Acids

Essential or Protein-Building (Proteinogenic) L-Amino Acids.

Amino acids are critical to nutrition and to life as a whole, and have a variety of roles in an organism's metabolism; one particularly important function is as the building blocks of proteins, which are polymers of amino acids. Amino acids are also important in many other biological molecules, such as forming parts of coenzymes or as precursors for the biosynthesis of molecules or production of energy. Proteinogenic amino acids are those 20 amino acids that are found in proteins and that are coded for in the standard genetic code. Proteinogenic amino acids (three-letter symbol/one-letter symbol) include L-alanine (Ala/A), L-arginine (Arg/R), L-asparagine (Asn/N), L-aspartic acid (Asp/D), L-cysteine (Cys/C), L-glutamic acid (Glu/E), L-glutamine (Gln/Q), glycine (Gly/G), L-histidine (H is/H), L-isoleucine (Ile/I), L-leucine (Leu/L), L-lysine (Lys/K), L-methionine (Met/M), L-phenylalanine (Phe/F), L-proline (Pro/P), L-serine (Ser/S), L-threonine (Thr/T), L-tryptophan (Trp/W), L-tyrosine (Tyr/Y) and L-valine (Val/V).

Non-proteinogenic amino acids are either not found in proteins (like gamma-aminobutyric acid aka GABA, L-Dopa) or not coded for in the standard genetic code (like hydroxyproline and selenomethionine), but can result from posttranslational modification of proteins.

Clinically Relevant Amino Acids.

Clinically relevant amino acids include all above described proteinogenic amino acids plus non-proteinogenic amino acids plus others including L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine, gamma-aminobutyric acid aka GABA, L-Dopa, hydroxyproline, selenomethionine, phosphoserine, gamma-aminoadipic acid, phosphoethanolamine, sarcosine, β-alanine, taurine, citrulline, beta-aminoisobutyric acid, carnosine, methyl histidine, alpha-aminobutyric acid, anserine, ethanolamine, cystathionine, hydroxylysine, ornithine, argininosuccinate, s-sulfocysteine, homocitrulline, hawkinsin. The methods and kits described herein are useful to identify or detect and/or quantitate any of the listed amino acids alone or in combination (see FIGS. 2 and 3).

Disorders Associated with Aberrant Amino Acid Levels

Aberrant Amino Acid Levels.

The presence, absence, identity, amount or modification of an endogenous amino acid as well as its presence and amount in comparison to other amino acids are important in assessing a subject's health and metabolic state. Aberrant amino acid levels or increased/decreased levels of certain amino acids in comparison to other amino acids can indicate a metabolic disturbance and can be used to diagnose metabolic and other disorders. For example, low plasma amino acid levels can indicate an inflammatory process in the body whose underlying cause might be cancer, alcohol abuse, malnutrition, Crohn's disease, infection and so forth. High plasma amino acid levels can indicate vitamin deficiencies (Vitamin C and D), diabetes mellitus, liver damage, heavy metal poisoning and more.

Metabolic Disorders.

The quantitative analysis of amino acids in biological fluids and tissues is instrumental in establishing a metabolic profile in order to detect disorders that are associated with changes in amino acid metabolism. Many metabolic disorders are inherited and require a rapid and reliable diagnosis and appropriate treatment or dietary changes to avoid irreversible harm of organs or the central nervous system. Metabolic disorders may result from primary amino acid enzymopathies and/or disorders of amino acid transport and/or processing. Primary amino acid enzymopathies are generally characterized by abnormal functioning or lack of a particular enzyme needed to metabolize one or more amino acids.

Phenylketonuria (PKU) is among the most common inherited metabolic disorders, where the lack of the enzyme phenylalanine hydroxylase leads to an accumulation of the amino acid phenylalanine and its metabolites. Elevated phenylalanine levels and levels of related metabolites (phenylketones) irreversibly impair brain development and can cause mental retardation, brain damage and seizures; symptoms are avoided if dietary restriction of phenylalanine is implemented very early in life and maintained lifelong. Therefore, presymptomatic identification of PKU infants via newborn screening is performed in all states in the US and in all developed countries worldwide.

Maple syrup urine disease (MSUD) is characterized by an accumulation of the branched-chain amino acids (BCAA) leucine, isoleucine and valine due to mutations of components of the branched-chain α-ketoacid dehydrogenase (BCKD) multienzyme complex that typically catalyzes the oxidative decarboxylation of branched-chain α-ketoacids (BCKA) derived from the BCAA. MSUD manifests clinically with fatal acidosis, neurological derangement and mental retardation (A Evarsson et al., 2000).

Galactosemia can lead to brain and liver damage and is characterized by an accumulation of galactose 1-phosphate due to the body's inability to metabolize the simple sugar galactose, lacking one or more of the liver enzymes galactose-1 phosphate uridyl transferase, galactose kinase, or galactose-6-phosphate epimerase. Subjects with galactosemia can have abnormal excretion of amino acids in their urine (generalized aminoaciduria) reflecting kidney damage caused by elevated galactose metabolites.

Homocystinuria is characterized by high levels of homocysteine due to the lack of the enzyme cystathionine beta-synthase, which facilitates the metabolism of the amino acid methionine and becomes clinically apparent in visual impairment, deformities of chest and spine, mental retardation and increased risk for blood clots.

Glutaric acidemia type 1 is an inherited disorder in which the body is unable to entirely break down the amino acids lysine, hydroxylysine and tryptophan. Excessive levels of their intermediate breakdown products can accumulate and damage the brain, particularly the basal ganglia, which are regions that help regulate movement.

Citrullinemia is an inherited metabolic condition caused by gene mutations of one of the enzymes in the urea cycle. The urea cycle is the body's system for excreting ammonia and for synthesizing arginine and urea. Citrullinemia is characterized by abnormally low levels of arginine and elevated levels of citrulline, which is a key intermediate in the urea cycle. The impaired ability to detoxify ammonia through its conversion to urea leads without treatment to life-threatening hyperammonemia; the early detection in newborns and immediate treatment through dietary restriction is therefore extremely important.

Gyrate atrophy is a rare hereditary disease of the eye's retina and choroid and characterized by progressive loss of vision, with total blindness usually occurring at age 40 or older. Due to a defective enzyme, the amino acid ornithine from the urea cycle is not converted to glutamate, leading to increased levels of ornithine.

The molybdenum cofactor is essential for the function of several enzymes and the deficiency of this cofactor (molybdenum cofactor deficiency) is an often fatal genetic disorder that leads in affected patients to severe neurological damage and early death. There is currently no effective therapy. Molybdenum cofactor deficiency can be diagnosed by measuring urinary S-sulfocysteine, but the condition is often confused with ischemic encephalopathy and therefore likely under-diagnosed.

The Renal Fanconi Syndrome describes an array of renal tubular dysfunctions which can have both genetic and acquired causes and which, in general, are characterized by an impaired solute transport in the renal tubule cells, leading to glucosuria, hyperaminoaciduria, phosphaturia, renal tubular acidosis. In children, cystinosis is one of the most common causes of the Renal Fanconi Syndrome with cystine accumulating in lysosomes of renal tubule cells. The syndrome can be diagnosed by assessing intracellular cystine levels.

Newborn Screening.

Genetic testing in newborn infants currently includes both specific testing for clinical indications in neonates with apparent symptoms and routine newborn screening. Metabolic tests include analyses for amino acids, acylcarnitines, organic acids and carnitine to uncover metabolic disorders such as phenylketonuria, congenital hypothyroidism, sickle cell disease, galactosemia, maple syrup urine disease, homocystinuria, urea cycle defects, biotinidase deficiency, cystic fibrosis and congenital adrenal hyperplasia.

Renal Amino Acid Transport Disorders.

Cystinuria is an inherited metabolic disorder due to a gene mutation that prevents the reabsorption of cysteine (cystine) and dibasic amino acids from the renal tubules and intestinal tract. Cysteine (cystine) consequently accumulates and precipitates in the urinary tract, leading to stone formation and eventually renal insufficiency; elevated cysteine (cystine) levels can be measured in the urine.

Kits

Kits for use in practicing the subject invention are also provided. The subject kits might at least include a pair of chromatographic columns where one column is made from graphitic carbon and the other column is a reverse-phase column such as a C18-column, one or more deproteinizing agents and one or more suitable internal standards. The kit might further contain additional components such as reagents necessary for carrying out chromatographic separation and/or mass spectrometric detection.

The subject kits may also include written instructions for use in the above-described methods. The instructions may be printed on a substrate, such as paper or plastic, etc. As such, the instructions may be present in the kits as a package insert, in the labeling of the container of the kit or components thereof. The instructions may include software or algorithms for data visualization or data analysis as described above.

The subject kits may also include a computer-readable medium containing the above-described instructions, or means for accessing such instructions such as means for obtaining the algorithms from a remote source, e.g. via the Internet.

In many embodiments of the subject kits, the components of the kit are packaged in a kit containment element to make a single, easily handled unit.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

Detailed Description of an Embodiment of the Present Invention

The present invention features liquid chromatography-mass spectrometry methods and kits for the specific, sensitive and rapid detection as well as quantitation of free amino acids in biological fluids, tissues, and other sample matrices following High Pressure Liquid Chromatography (HPLC) separation. The methods and kits allow the reliable detection as well as quantitation of the clinically relevant amino acids, even the most non-polar ones, and find wide-spread application in various areas such as diagnosing metabolic disorders, therapeutic drug monitoring, drug screening, drug analysis and general sample testing to assess parameters such as purity of amino acids in a sample.

Amino Acids

The amino acids of the present invention include, but are not limited to, essential and proteinogenic amino acids that are found in proteins and that are coded for in the standard genetic codes; non-proteinogenic amino acids that are either not found in proteins (like gamma-aminobutyric acid aka GABA, L-Dopa) or not coded for in the standard genetic code (like hydroxyproline and selenomethionine), but can result from posttranslational modification of proteins and, generally, clinically relevant amino acids. Clinically relevant amino acids include all above described proteinogenic amino acids plus non-proteinogenic amino acids plus others including L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, gamma-aminobutyric acid aka GABA, L-Dopa, hydroxyproline, selenomethionine, phosphoserine, gamma-aminoadipic acid, phosphoethanolamine, sarcosine, β-alanine, taurine, citrulline, beta-aminoisobutyric acid, carnosine, methyl histidine, alpha-aminobutyric acid, anserine, ethanolamine, cystathionine, hydroxylysine, ornithine, argininosuccinate, s-sulfocysteine, homocitrulline, hawkinsin. The methods and kits described herein are useful to identify, detect and/or quantitate any of the listed amino acids alone or in combination (see FIGS. 2 and 3).

Sample

Any sample containing or suspected of containing an amino acid can be used, including a biological fluid consisting of or containing blood, serum, plasma, lymph fluid, amniotic fluid, saliva, cerebrospinal fluid, lacrimal fluid, mucus, urine, sputum, sweat, a combination thereof or a specimen from in-vitro cell culture or in-vivo testing in an experimental animal model. In other embodiments of the invention, the sample can be a biological tissue consisting of or containing skeletal muscle tissue, liver tissue, lung tissue, kidney tissue, myocardial tissue, brain tissue, or a combination thereof. Further samples within the scope of the present invention are research samples derived from studies including those of experimental animals that might be of mammalian or non-mammalian origin, cell culture products, tissue extracts, and synthetic mixtures and any other biological or non-biological samples that consist of or contain a food, food component or pharmacological agent and that might be analyzed for the purposes of assessing the purity of a sample and/or for assessing the concentration of amino-acid based ingredients.

In further embodiments, the amino acids in a sample can result following hydrolysis of a protein or peptide according to methods that are known in the art, for example, by incubating a sample containing a protein or peptide with boiling aqueous acids, such as hydrochloric acid, or bases.

Deproteinization to Produce Free Amino Acids

All samples, as used in the present invention, are deproteinated prior to analysis. This can be achieved with conventional methods known to those skilled in the art. For example, a sample can be deproteinated with acetonitrile or methanol/acetonitrile mixture, with or without containing an internal standard, followed by vortexing and centrifugation. In embodiments of the present invention, a methanol:acetonitrile mixture was used in the ratio of 3:1.

Chromatographic Separation

Following deproteinization, the free amino acids are separated by liquid chromatography, as described in the experimental section, using reverse-flow conditions on a pair of chromatographic columns. Important aspects of the present invention are the removal of negatively-charged interferents at the initial part of the chromatographic separation using a first column with graphitic carbon architecture and the application of reverse-flow conditions to achieve retrograde elution of the amino acids off the first column onto a second column which may be a standard reverse-phase column such as a C18-column. In embodiments of the present invention, a porous graphite carbon column was used as the first column (column 1, Thermo Fisher Scientific, 5 μm Hypercarb, 2.1 mm ID×50 mm), while a fused-core C18-column was used as the second column (column 2, Advanced Materials Technology, 2.7 μm Halo C18, 2.1 mm ID×100 mm).

Introduction of Amino Acids into a Mass Spectrometer and Ionization

Following separation by liquid chromatography (LC), the free amino acids, in the LC eluate, are introduced into a mass spectrometer and subjected to ionization. Various ionization techniques can be used. For example, photoionization, electrospray ionization (ESI), atmospheric pressure chemical ionization (APCI), and electron capture ionization may be used. Preferably, electrospray ionization is used in embodiments of the present invention.

Ionization may be performed by operating the mass spectrometer in the negative or positive mode. The following mass spectrometers can be used in embodiments of the present invention: any tandem mass spectrometer including ion trap mass spectrometers and liquid chromatography-mass spectrometers such as API 2000™, API 3000™ or API 4000™ mass spectrometer, as described in U.S. Pat. Nos. 5,179,278; 5,847,386 and 5,420,425. In embodiments of the present invention, an API 3000™ with Turbulon Ion Spray source (electrospray ionization) was used in the positive mode.

Amino acids are identified on the basis of the mass to charge ratio (m/z ratio) of their molecular ions and fragment ions, as known to those skilled in the art. In addition, following separation by liquid chromatography, the amino acids or fragments thereof can also be identified by their retention times.

When using tandem mass spectrometry, the amino acids are sent through a first mass spectrometer, where they are fragmented through collision-induced dissociation, and then sent through a second mass spectrometer to obtain a characteristic set of fragment peaks from the amino acids, which then are analyzed using appropriate amino acid identification software and algorithms such as Analyst Software™, Applied Biosystems. In embodiments of the present invention, Analyst Software Version 1.4. was utilized.

Amino acids or their fragments are quantified according to their peak intensity or peak area, as determined in the mass spectrometer in counts per second.

Experimental Procedures

The following methods and materials were used in the example that is described further below.

Reagents.

Amino acid standards were obtained from Sigma-Aldrich (St. Louis, Mo.) and Wako Chemicals USA, Inc (Richmond, Va.). L-Homocitrulline was obtained from Advanced Asymmetrics, Inc. (Millstadt, Ill.), and HPLC-grade acetonitrile and methanol from Honeywell Burdick & Jackson (Morristown, N.J.).

Preparation of Calibration Mixtures and Standards.

Calibration Standards were Prepared by mixing Amino Acids Mixture Standard Solutions, Type AN-2 and Type B (Wako) and 2 mM TDFHA together with stock solutions of tryptophan, glutamine, asparagine, alloisoleucine, homocitrulline and homocystine that were prepared from weighed standards. This stock was diluted with 2 mM TDFHA to final concentrations used for calibration.

Instrumentation.

The analytical apparatus consisted of a Shimadzu solvent delivery apparatus (model LC-10ADvp pumps and SCL-10Avp controller), LEAP Technology autosampler (model HTS PAL) and API 3000 Tandem Mass Spectrometer with Turbulon Ion Spray source (Applied Biosystems Inc., Foster City, Calif.). Nitrogen was delivered to the analytical apparatus by a liquid nitrogen Dewar. Chromatographic separation was achieved using a series of two columns, Column 1, a porous graphitic carbon (PGC) column (Thermo Fisher Scientific, 5 μm Hypercarb, 2.1 mm ID×50 mm), and Column 2, a fused-core column (Advanced Materials Technology, 2.7 μm Halo C18, 2.1 mm ID×100 mm). Column 2 was maintained at 43° C. using a Hot Pocket (Thermo Hypersil-Keystone, Bellefonte, Pa.). The two columns were connected through a 10-port switching valve (Valco Instruments Co. Inc, Houston, Tex.).

EXAMPLES

The following example is put forth so as to provide those of ordinary skill in the art with a complete disclosure and description of how to make and use the present invention; it is not intended to limit the scope of what the inventors regard as their invention. Unless indicated otherwise, part are parts by weight, molecular weight is average molecular weight, temperature is in degrees Centigrade, and pressure is at or near atmospheric.

Example 1

Qualitative and Quantitative Analysis of Underivatized Amino Acids by Liquid Chromatography-Tandem Mass Spectrometry (LC-MS/MS) Following Ion Pairing Chromatography This example describes the analysis of underivatized amino acids by LC-MS/MS with short analysis time, high sensitivity and specificity, and baseline resolution of structural isomers. Separation of amino acids was achieved using a series of two chromatographic columns, the first for sample clean-up and elimination of interfering substances, and the second for the actual separation of compounds. The total run time including re-equilibration was 15 min per sample.

Samples.

Plasma, urine and cerebrospinal fluid (CSF) samples were obtained as residual, anonymized specimens from the Stanford Clinical Laboratories with IRB approval. Samples (30 μL) were deproteinized with 90 μL methanol:acetonitrile (3:1), incubated at room temperature for 5 min, and centrifuged for 5 min at 15,000 rpm. Supernatants (20 μL) were diluted with 380 μL of 2 mM tridecafluoroheptanoic acid (TDFHA) containing 2.04 μM of S-amino-ethylcysteine (SAEC) as internal standard, and transferred to autosampler vials for analysis.

Chromatography and Amino Acid Quantitation.

A volume of 100 of sample was introduced via an autosampler into the mobile phase of 1 mM TDFHA in water at a flow rate of 0.1 mL/min (FIG. 1). During the first 1.5 minutes, Column 2 was switched offline, allowing negatively-charged interferents to be eluted to waste. At 1.5 min, the valve was switched to bring Column 2 inline with Pump A (1 mM TDFHA acid in water) and Pump B (1 mM TDFHA in acetonitrile) at a total flow rate of 0.2 ml/min.

At the same time, the direction of solvent flow was reversed; this resulted in the retrograde elution amino acids off of Column 1 using a gradient which continued into Column 2 for analytical separation. Specific gradient conditions are shown in Table 1. All amino acids were analyzed in the positive ion mode and detected by selected reaction monitoring (SRM). Instrument parameters were optimized for each amino acid by infusing individual standards of weighed molecules at a concentration of 0.05 μmol/ml and flow rate of 100/min. Specific ion transitions and instrument parameters are detailed in Table 2. Data were acquired using Analyst software version 1.4, and exported to Excel (2002 edition, Microsoft Corporation) for further calculations. Chromatographic peaks were manually inspected to ensure that baselines were correctly drawn. Quantitative values were obtained by relating chromatographic peak areas to those derived from externally run calibration standards at concentration levels of 10, 100, 250, 500, 750 and 1000 nmol/ml using s-aminoethylcystine (SAEC) as the internal standard.

TABLE 1

Chromatographic conditions for amino acid analysis.

| Time (min) | Buffer A (%) | Buffer B (%) |
| --- | --- | --- |
| 0.00 (START) | 86 | 14 |
| 1.55 | 86 | 14 |
| 8.00 | 65 | 35 |
| 9.40 | 55 | 45 |
| 9.60 | 0 | 100 |
| 10.20 | 86 | 14 |
| 15.00 (END) | | |

Buffer A, 1 mM TDFHA acid in water;
Buffer B, 1 mM TDFHA in 100% acetonitrile.
Prior to 1.5 min the mobile phase was pumped through the first column and diverted to waste; a switching valve was turned to bring the second column inline at 1.5 min and offline at 10.1 min.

TABLE 2

Ion transitions and instrument parameters for amino acid detection

| | Ion Transitions | DP[a] | FP | CE | CXP | Dwell Time | RT |
| --- | --- | --- | --- | --- | --- | --- | --- |
| Alanine | 90.0 > 44.2 | 29 | 150 | 19 | 7 | 11 | 3.9 |
| β-Alanine | 90.0 > 72.0 | 29 | 150 | 12 | 6 | 11 | 6.1 |
| Alloisoleucine | 132.2 > 86.1 | 27 | 140 | 15 | 4 | 11 | 6.9 |
| Arginine | 175.2 > 70.0 | 27 | 140 | 30 | 12 | 11 | 9.6 |
| Asparagine | 133.2 > 116.0 | 30 | 160 | 14 | 7 | 11 | 3.2 |
| Aspartate | 134.2 > 88.2 | 29 | 150 | 15 | 8 | 11 | 3.0 |
| Citrulline | 176.3 > 159.2 | 27 | 140 | 15 | 9 | 11 | 3.8 |
| Cystathionine | 223.1 > 134.0 | 27 | 140 | 21 | 7 | 11 | 4.4[b] |
| Cysteine | 122.1 > 76.0 | 29 | 150 | 18 | 6 | 11 | 3.6 |
| Cystine | 241.0 > 74.0 | 29 | 150 | 18 | 6 | 11 | 3.6 |
| Ethanolamine | 62.0 > 44.0 | 24 | 140 | 16 | 7 | 20 | 6.2 |
| Glutamate | 148.3 > 130.1 | 30 | 150 | 14 | 11 | 11 | 3.5 |
| Glutamine | 147.1 > 130.1 | 28 | 130 | 14 | 7 | 11 | 3.4 |
| Glycine | 76.1 > 30.1 | 35 | 190 | 18 | 4 | 80 | 3.5 |
| Histidine | 156.3 > 110.2 | 26 | 140 | 20 | 10 | 11 | 9.1 |
| Homocitrulline | 190.1 > 173.0 | 31 | 170 | 15 | 10 | 11 | 4.3 |
| Homocystine | 269.2 > 136.2 | 28 | 130 | 15 | 7 | 11 | 9.5 |

TABLE 2-continued

Ion transitions and instrument parameters for amino acid detection

|  | Ion Transitions | DP[a] | FP | CE | CXP | Dwell Time | RT |
|---|---|---|---|---|---|---|---|
| Hydroxyproline | 132.1 > 86.1 | 27 | 140 | 15 | 4 | 11 | 3.1 |
| Isoleucine | 132.1 > 86.1 | 27 | 140 | 15 | 4 | 11 | 7.3 |
| Leucine | 132.2 > 86.1 | 27 | 140 | 15 | 4 | 11 | 7.7 |
| Lysine | 147.1 > 130.1 | 28 | 130 | 14 | 7 | 11 | 9.6 |
| Methionine | 150.3 > 133.1 | 29 | 140 | 14 | 7 | 11 | 5.4 |
| Ornithine | 133.2 > 116.0 | 30 | 160 | 14 | 7 | 11 | 9.3 |
| Phenylalanine | 166.1 > 120.0 | 26 | 150 | 20 | 6 | 11 | 8.0 |
| Proline | 116.0 > 70.0 | 29 | 150 | 21 | 6 | 11 | 3.8 |
| S-AEC | 165.4 > 120.1 | 26 | 120 | 19 | 6 | 11 | 8.7 |
| Sarcosine | 90.0 > 44.2 | 29 | 150 | 19 | 7 | 11 | 3.4 |
| Serine | 106.1 > 60.0 | 34 | 150 | 17 | 5 | 11 | 3.3 |
| Sulfocysteine | 202.1 > 120.0 | 39 | 190 | 18 | 6 | 11 | 2.6 |
| Taurine | 126.0 > 108.0 | 39 | 175 | 16 | 5 | 11 | 2.8 |
| Threonine | 120.3 > 74.0 | 29 | 150 | 16 | 6 | 11 | 3.6 |
| Tryptophan | 205.1 > 188.0 | 24 | 120 | 13 | 11 | 11 | 9.0 |
| Tyrosine | 182.0 > 136.2 | 28 | 150 | 18 | 7 | 11 | 5.6 |
| Valine | 118.1 > 72.1 | 29 | 150 | 16 | 6 | 11 | 5.4 |

[a]DP, declustering potential; FP, focusing potential; CE, collision energy; CXP, collision cell exit potential; RT, retention time
[b]Doublet peak Precision and Linearity:

Mixtures of amino acid standards were prepared in 0.01N HCl and diluted to 10, 100, 250, 500, 750 and 1000 nmol/ml with 2 mM TDFHA. Each solution was analyzed five times in a single batch, as well as in singlicate over ten days. Representative data for the lowest, middle and highest concentration levels are shown in Table 3; all other levels showed comparable variation (data not shown). The average within-run precision was 4.4% for all amino acids and concentration levels, with the highest imprecision (9.7%) representing glycine at 10 nmol/ml. The average between-run precision was 4.6%, with higher variability for glutamine (25.9% at the 1000 nmol/ml level) reflecting a decreased response over time from compound instability. All amino acids showed excellent linearity over the range of 10-1000 nmol/ml, with correlations ranging from 0.981 (serine and proline) to 0.998 (cystathionine). The concentration range was extended to 2000 nmol/ml for most amino acids with good fit using the Wagner regression (data not shown). The average variability in retention time variability was 0.2% for all amino acids, and has remained stable for at over 5,000 injections.

TABLE 3

Within-run precision, between-run precision and linearity of amino acid quantitation

|  | Within-run precision* | | | Between-run precision** | | | |
|---|---|---|---|---|---|---|---|
|  | 10 μM | 500 μM | 1000 μM | 10 μM | 500 μM | 1000 μM | R |
| Alanine | 7.4 | 4.7 | 4.2 | 12.4 | 4.7 | 5.9 | 0.990 |
| β-Alanine | 4.6 | 5.2 | 4.5 | 9.4 | 7.7 | 8.4 | 0.996 |
| Alloisoleucine | 4.5 | 4.9 | 3.4 | 10.9 | 8.1 | 4.0 | 0.993 |
| Arginine | 7.3 | 5.8 | 4.0 | 15.3 | 10.2 | 11.2 | 0.997 |
| Asparagine | 7.6 | 3.0 | 2.3 | 3.4 | 0.0 | 0.4 | 0.987 |
| Aspartate | 7.3 | 3.3 | 1.4 | 11.5 | 4.6 | 7.3 | 0.992 |
| Citrulline | 5.5 | 3.6 | 4.1 | 16.6 | 1.6 | 3.6 | 0.991 |
| Cystathionine | 3.1 | 1.6 | 4.0 | 14.9 | 7.7 | 6.8 | 0.998 |
| Cystine | 9.3 | 3.9 | 2.0 | 10.3 | 4.3 | 2.1 | 0.994 |
| Ethanolamine | 3.7 | 4.8 | 4.8 | 5.8 | 10.4 | 4.3 | 0.995 |
| Glutamate | 3.5 | 3.5 | 3.4 | 0.6 | 0.2 | 1.3 | 0.991 |
| Glutamine | 4.0 | 1.5 | 1.5 | 0.3 | 31.2 | 25.9 | 0.994 |
| Glycine | 9.7 | 4.3 | 2.5 | 2.5 | 6.6 | 3.8 | 0.984 |
| Histidine | 5.1 | 5.0 | 3.0 | 0.3 | 3.8 | 2.8 | 0.988 |
| Homocitrulline | 4.9 | 4.9 | 3.6 | 11.0 | 8.8 | 10.7 | 0.995 |
| Homocystine | 3.5 | 5.1 | 5.6 | 4.3 | 1.0 | 3.5 | 0.997 |
| Hydroxyproline | 4.2 | 3.5 | 2.6 | 8.9 | 1.1 | 0.1 | 0.993 |
| Isoleucine | 6.7 | 5.8 | 3.5 | 6.0 | 6.2 | 2.7 | 0.994 |
| Leucine | 4.5 | 5.5 | 3.9 | 1.8 | 4.8 | 3.5 | 0.995 |
| Lysine | 6.6 | 5.5 | 4.7 | 4.3 | 0.3 | 1.7 | 0.997 |
| Methionine | 4.5 | 4.7 | 6.0 | 13.0 | 12.3 | 7.0 | 0.993 |
| Ornithine | 7.1 | 5.6 | 3.5 | 4.8 | 0.7 | 0.8 | 0.997 |
| Phenylalanine | 6.0 | 3.5 | 2.9 | 0.4 | 2.8 | 2.0 | 0.992 |
| Proline | 7.1 | 3.6 | 2.3 | 12.9 | 0.1 | 1.5 | 0.981 |
| Sarcosine | 5.5 | 3.3 | 2.4 | 7.0 | 5.4 | 1.6 | 0.991 |
| Serine | 4.0 | 3.1 | 2.9 | 6.9 | 3.2 | 1.4 | 0.981 |
| Taurine | 4.0 | 2.7 | 1.7 | 6.4 | 0.7 | 2.1 | 0.993 |
| Threonine | 4.4 | 3.6 | 2.5 | 5.3 | 2.8 | 4.5 | 0.985 |
| Tryptophan | 7.4 | 4.2 | 4.6 | 6.3 | 4.1 | 1.1 | 0.995 |

TABLE 3-continued

Within-run precision, between-run precision and linearity of amino acid quantitation

|  | Within-run precision* | | | Between-run precision** | | | |
| --- | --- | --- | --- | --- | --- | --- | --- |
|  | 10 μM | 500 μM | 1000 μM | 10 μM | 500 μM | 1000 μM | R |
| Tyrosine | 4.8 | 3.9 | 4.4 | 11.8 | 14.7 | 9.0 | 0.997 |
| Valine | 4.6 | 4.7 | 4.3 | 13.1 | 8.6 | 5.3 | 0.987 |

*n = 5 for each amino acid and concentration level
**each point represents determinations over n days Discussion.

Using the first chromatographic column flow-reverse proved beneficial in delaying the elution of hydrophilic amino acids and in improving their ionization in the mass detector, leading to increased analytical sensitivity. In addition, acetonitrile conditions favor the improved chromatographic resolution of isomeric compounds (alloisoleucine, isoleucine, and leucine) in the second column.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

A Evarsson A et al. (2000). Crystal structure of human branched-chain α-ketoacid dehydrogenase and the molecular basis of multienzyme complex deficiency in maple syrup urine disease. *Structure* 8:277-291.

Bruins A P. (1999). Mechanistic aspects of electrospray ionization. *J. Chromatography A* 794:345-357.

Casetta B et al. (2000). Development of a method for rapid quantitation of amino acids by liquid chromatography-tandem mass spectrometry in plasma. *Clin Chem Lab Med* 38:391-401.

Dietzen D J et al. (2008). Rapid comprehensive amino acid analysis by liquid chromatography/tandem mass spectrometry: comparison to cation exchange with post-column ninhydrin detection. *Rapid Commun Mass Spectrom* 22:3481-3488.

Fernandes J et al. (1990). Inborn metabolic diseases: diagnosis and treatment. Berlin, New York, Springer, 1st edition, pp. 5-6.

Freeto S et al. (2007). A rapid ultra performance liquid chromatography tandem mass spectrometric method for measuring amino acids associated with maple syrup urine disease, tyrosinaemia and phenylketonuria. *Ann Clin Biochem* 44:474-481.

Lim C K (1989). Electronic interaction chromatography on porous graphitic carbon. Separation of [99mtc]pertechnetate and perrhenate anions. *Biomedical Chromatography* 3(2):92-93.

Piraud M et al. (2003). ESI-MS/MS analysis of underivatised amino acids: a new tool for the diagnosis of inherited disorders of amino acid metabolism. Fragmentation study of 79 molecules of biological interest in positive and negative ionisation mode. *Rapid commun in mass spectrom* 17:1297-1311.

Piraud M et al. (2005a). Ion-pairing reversed-phase liquid chromatography/electrospray ionization mass spectrometric analysis of 76 underivatized amino acids of biological interest: a new tool for the diagnosis of inherited disorders of amino acid metabolism. *Rapid commun in mass spectrom* 19:1587-1602.

Piraud M et al. (2005b). A new reversed-phase liquid chromatographic/tandem mass spectrometric method for analysis of underivatised amino acids: evaluation for the diagnosis and the management of inherited disorders of amino acid metabolism. *Rapid commun in mass spectrom* 19:3287-3297.

Spackman D H et al. (1958). Automatic Recording Apparatus for Use in Chromatography of Amino Acids. *Anal Chem* 30:1190-1206.

What is claimed is:

1. A method of analyzing a sample suspected of containing free amino acids using liquid chromatography-mass spectrometry, comprising:
   preparing a sample to obtain free amino acids;
   separating the free amino acids by liquid chromatography using a series of at least two chromatographic columns including (a) a first chromatographic column including a graphitic carbon packing material to separate negatively-charged interferents from the free amino acids, followed by (b) a second, reversed phase, solid core chromatographic column to separate the free amino acids from one another, wherein separating the free amino acids includes eluting the free amino acids off the first chromatographic column in a flow-reverse direction into the second chromatographic column;
   ionizing the sample to generate ions;
   fragmenting the ions to produce parent and daughter ions;
   detecting the parent and daughter ions by selected reaction monitoring (SRM); and
   detecting the presence of the free amino acids in accordance to the detected parent and daughter ions.

2. The method of claim 1, wherein the sample is a biological fluid, and preparing the sample includes deproteinizing the sample.

3. The method of claim 1, wherein separating the free amino acids using the first chromatographic column includes separating the negatively-charged interferents from any taurine in the sample.

4. The method of claim 1, wherein the second chromatographic column is selected from a C18-column and a C8-column.

5. The method of claim 1, wherein separating the free amino acids using the second chromatographic column includes separating isomeric amino acids from one another.

6. The method of claim 5, wherein separating the isomeric amino acids from one another includes separating any alloisoleucine, isoleucine, and leucine in the sample.

7. The method of claim 1, wherein separating the free amino acids using the first chromatographic column includes separating chloride ion from the free amino acids.

8. The method of claim 1, wherein separating the free amino acids includes eluting the free amino acids through the first chromatographic column in an isocratic mode, followed by retrograde elution of the free amino acids back through the first chromatographic column and through the second chromatographic column in a gradient mode.

9. The method of claim 1, wherein eluting the free amino acids off the first chromatographic column in the flow-reverse direction into the second chromatographic column is performed in a gradient mode.

10. The method of claim 9, wherein eluting in the gradient mode includes eluting in a decreasing amount of water.

11. The method of claim 9, wherein eluting in the gradient mode includes eluting in an increasing amount of acetonitrile.

12. The method of claim 1, further comprising quantifying the free amino acids in accordance to the detected parent and daughter ions.

* * * * *